United States Patent [19]
Gebert

[11] Patent Number: 5,468,228
[45] Date of Patent: Nov. 21, 1995

[54] INTRAVENOUS CANNULA CONNECTOR

[76] Inventor: Rowan D. Gebert, 21 Cumberland Street, Eaglemont, Victoria, 3084, Australia

[21] Appl. No.: 244,579
[22] PCT Filed: Nov. 27, 1992
[86] PCT No.: PCT/AU92/00638
   § 371 Date: May 27, 1994
   § 102(e) Date: May 27, 1994
[87] PCT Pub. No.: WO93/10848
   PCT Pub. Date: Jun. 10, 1993

[30] Foreign Application Priority Data

Nov. 29, 1991 [AU] Australia .................................. PK9751
Mar. 16, 1992 [AU] Australia .................................. PL1371

[51] Int. Cl.⁶ ........................ A61M 39/00; A61M 25/02
[52] U.S. Cl. .................. 604/174; 128/DIG. 26; 604/177
[58] Field of Search ....................... 604/174, 177, 604/263, 165; 128/DIG. 26

[56] References Cited

U.S. PATENT DOCUMENTS

| | | | |
|---|---|---|---|
| 3,670,727 | 6/1972 | Reiterman | 604/177 |
| 4,352,354 | 10/1982 | Ujihara | 604/177 |
| 4,353,369 | 10/1982 | Muetterties et al. | 128/DIG. 26 |
| 4,362,156 | 10/1982 | Feller, Jr. et al. | 604/177 |
| 4,366,817 | 1/1983 | Thomas | 604/174 |
| 4,676,783 | 6/1987 | Jagger et al. | 604/177 |
| 4,737,143 | 4/1988 | Russell | 604/180 |
| 4,863,432 | 9/1989 | Kualo | 604/177 |
| 4,888,001 | 12/1989 | Schoenberg | 604/263 |
| 4,944,731 | 7/1990 | Cole | 604/263 |
| 5,084,032 | 1/1992 | Kornberg et al. | 604/192 |
| 5,147,319 | 9/1992 | Ishikawa et al. | 604/174 |
| 5,322,512 | 6/1994 | Mohiuddin | 604/177 |

OTHER PUBLICATIONS

International Search Report, Nov. 27, 1992.

Primary Examiner—Paul J. Hirsch
Attorney, Agent, or Firm—Arnold White & Durkee

[57] ABSTRACT

Disclosed is an intravenous cannula connector for connection of a cannula to a syringe or intravenous drip feed. The cannula has a central portion that allows fluid to pass through that is flanked by a pair of solid arm portions, each connected to a lateral wing portion. The wing portions sit laterally and forward relative to the central portion corresponding with the socket end of the cannula. The connector may be fixed in a non-detachable manner to the lower end of an intravenous set or to other syringe or intravenous attachments.

22 Claims, 7 Drawing Sheets

INTRAVENOUS CANNULA CONNECTOR

This invention relates to devices for intravenous infusion of fluids such as by drip-feed, anaesthesia and the like or sampling of blood, and more particularly relates to an intravenous cannula connector and fixation device.

A problem with administering intravenous medicinal fluids such as drip-feed and anaesthetic through tubing from a syringe or reservoir is that of cutaneous fixation of an intravenous cannula and this problem is aggravated by uncooperative patients or children, who can be very restless.

A disadvantage of standard intravenous cannulae is that they are not easy to secure to the skin because of the small surface: contact area of the device available for fixing by the use of adhesive tape and dressing and it is often necessary to use several pieces of adhesive tape. Furthermore, intravenous cannulae, when left in situ for long periods can cause pressure points on the skin.

A disadvantage of winged cannulae is that, whilst they have wings on the cannula itself to improve the surface contact and fixation with the skin, they are bulky ungainly and can be awkward to insert. They usually require a syringe to be attached in a rigid, inflexible manner, often perpendicular to the skin. This has the disadvantages that firstly, a syringe attached in a rigid, perpendicular manner is at risk of catching on drapes, bedding, etc. when a limb is moved and this can result in the entire device becoming dislodged; and secondly, a syringe attached in this manner can be difficult to detach from the cannula with one hand without dislodging the cannula.

A disadvantage of winged needle devices is that the portion remaining in the patient is a needle, not a cannula, and thus prone to migrate out of the vein into which it has been inserted.

A disadvantage of spigot-fit connections is that there is a risk of the cannula becoming disconnected from its spigotted connection. Screw-on, "luer-lock" type connections can be awkward to apply to a cannula in an uncooperative patient.

It is the object of this invention to provide an intravenous cannula connector which at least partly alleviates one or more of the foregoing problems and/or disadvantages.

According to the invention, there is provided an intravenous cannula connector for fixing an intravenous cannula in position on the skin after intravenous insertion of the cannula to leave an end portion of the cannula extending externally, the cannula connector having a body portion adapted at one end to couple to the end portion of the cannula to then provide for fluid flow to or from the cannula via the cannula connector, the cannula connector having, extending from the body portion at opposite sides thereof, respective wings which extend forwardly of the body portion beyond said end of the body portion to permit the cannula connector, when coupled to the cannula, to be affixed to the skin by a single piece of adhesive tape which extends over the wings and/or cannula to hold them substantially flat against the skin. Structure may be provided on the cannula connector wings, to improve the quality of attachment of a spigot connection to the cannula, to reduce the likelihood of disconnection.

The body may have one end thereto formed into a spigot, luer lock or the like for placement thereon of the cannula. The other end may be connected either to an intravenous giving set, or to any one of a number of standard intravenous or syringe attachments, such as a three-way tap, a non-return injection valve, or a plain luer attachment or the like, with or without a length of flexible tubing between the connector and the attachment. The wings may be flexible. Preferably the wings arc so set forward relative to the body as to in use of the connector be disposed in the same plane on either side of the body of the connector to leave a space therebetween for accommodating the cannula. The body and wing, when attached to the cannula, may together provide a large surface area in use in contact with the skin, which will not only facilitate fixation with adhesive tape, but will also assist in reducing pressure effects on the skin from the cannula.

The inside of the wings may be adapted, by way of a barbed step, a ratchet-type grip, or a textured prominence on the inside of the wings, to grip the cannula around the proximal end of the socket, thereby improving the attachment of a spigot to the cannula socket, and making disconnection less likely.

The ability to attach the connector and cannula to the skin of a patient by a single piece of adhesive tape enables easy stabilisation and fixation and the prevention of dislodgment of the cannula during use.

In some embodiments of the invention, there may be a length of flexible tubing fined non-detachably between the connector and anyone of several intravenous or syringe attachments, such as a three-way tap, a non-return injection valve, or a plain female luer attachment or the like. This flexible tubing, when present will afford a less rigid attachment between a syringe and the connector and reduce the risk of dislodgment of the cannula during manipulation or movement of the syringe.

Some non-limiting examples of embodiments or practical applications of the winged cannula connector of the invention will now be described with reference to the accompanying drawings in which.

Figure 1:
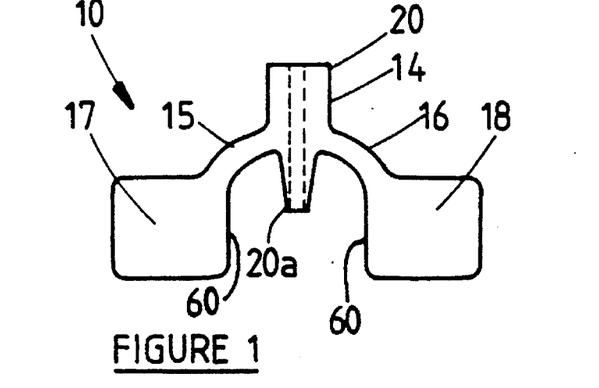
FIG. 1 is a plan view of one embodiment of the cannula connector of the present invention.
Figure 2:
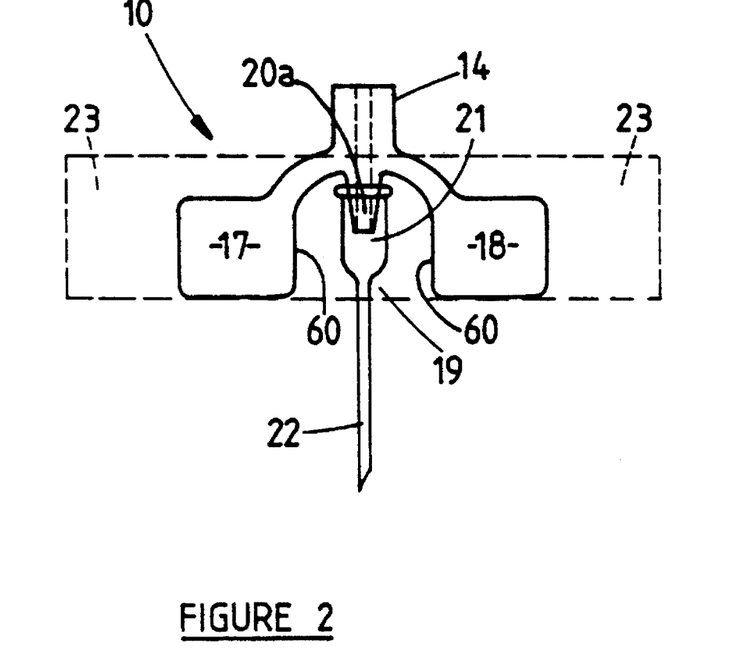
FIG. 2 is a plan view of the winged cannula connector attached to a cannula.

Referring to the drawings there is shown in FIGS. 1 and 2 one embodiment of a winged cannula connector 10 according to the invention. The winged cannula connector 10 is manufactured of any suitable flexible or pliable synthetic polymeric material such as polyethylene and manufactured by any suitable technique, such as injection moulding. The central portion 14 is connected via two lateral integral and solid arm portions 15, 16 to two integral and solid flexible wings 17, 18 which are set forward relative to the central portion. The central portion 14 has a hub portion 20 stepped down into a narrower diameter spigot or luer lock connector portion 20a for attachment thereto of the socket end 21 of a cannula 19 after the cannula has been inserted intravenously, the patient end 22 of the cannula lying in the vein beneath the skin. That is, the portion 20a is a tapered male portion adapted to seat in a corresponding tapered female opening in the cannula. Wings 17, 18 are disposed in the same plane, and each has an inside edge 60 which edges 60 are spaced from connector portion 20a to form a space around the portion 20a to accommodate the cannula when attached to portion 20a.

In FIG. 2 the cannula 19 is shown connected to the winged cannula connector 10. A liquid flow passage extends through both hub and spigot portions of the winged cannula connector. The two flexible wings 17, 18 of the winged cannula connector 10 are preferably formed integrally with the connector and are adapted to facilitate taping of the cannula connector to the skin of a patient using a single piece of adhesive tape 23 to hold the standard cannula 19 in place after it has been inserted into the vein of the patient, thereby preventing accidental dislodgment during administration of fluids or anaesthesia, or withdrawal of blood.

Figure 3:
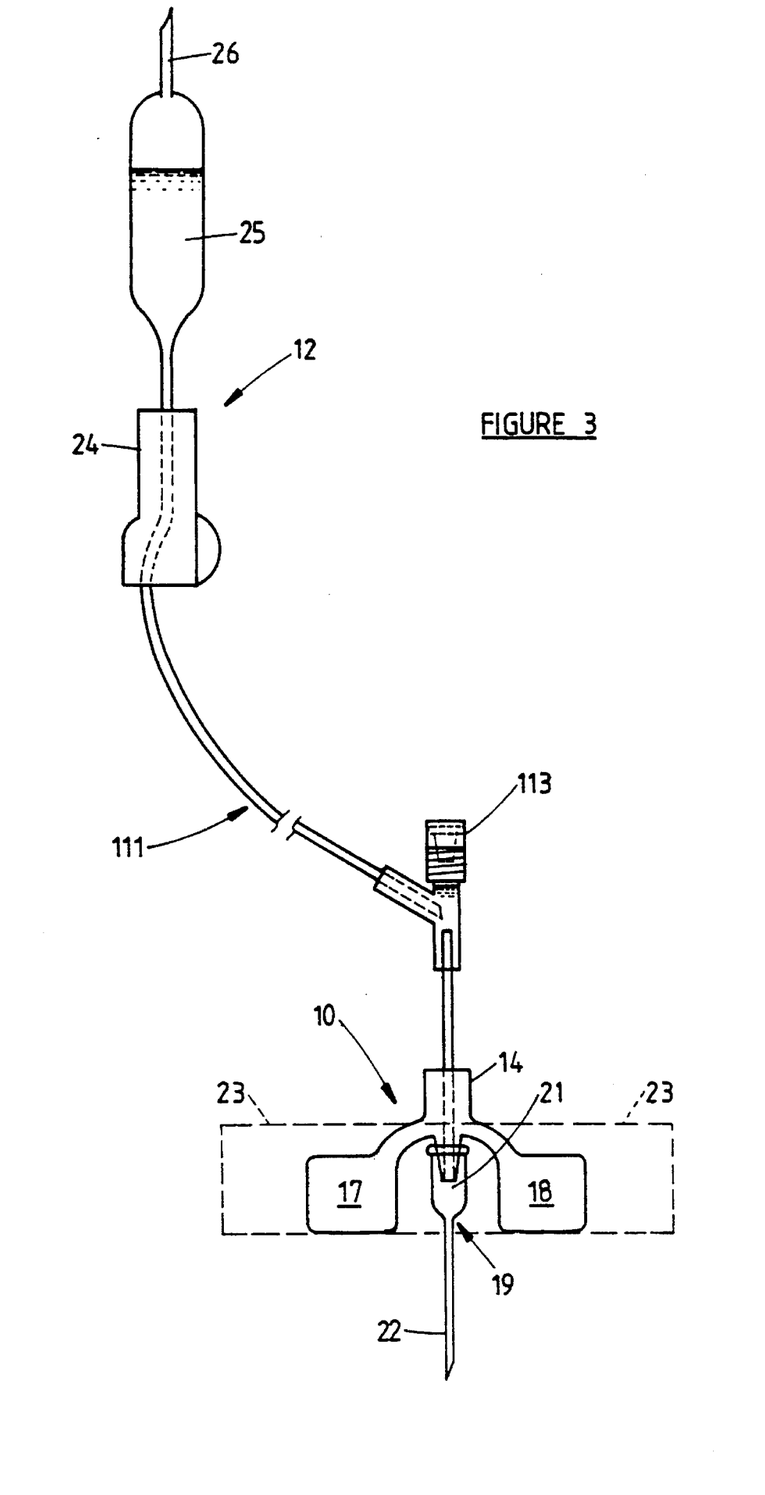
FIG. 3 is a plan view of a winged cannula connector fixed non-detachably to an intravenous giving set.

FIG. 3 shows an alternative application of the winged cannula connector 10, the connector being fixed non-detachably to the lower end of a standard intravenous giving set 12 which consists of flexible plastic tubing 111 an injection port 113, a flow regulator 24 and a drip chamber 25 with spiked bag penetrating end 26.

Figure 4:
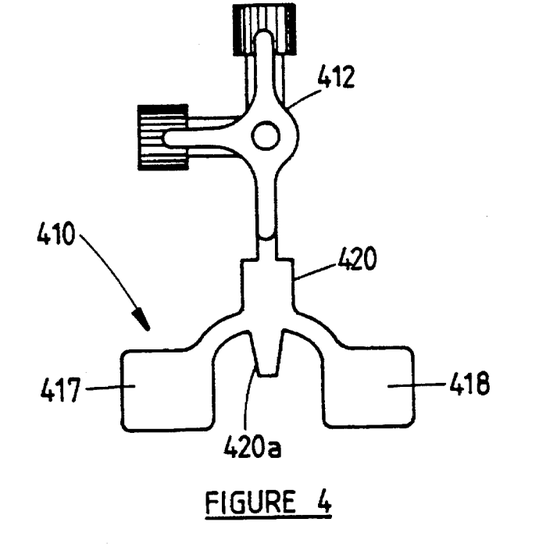
FIG. 4 is a plan view of a winged cannula connector fixed non-detachably to a three-way tap.
Figure 5:
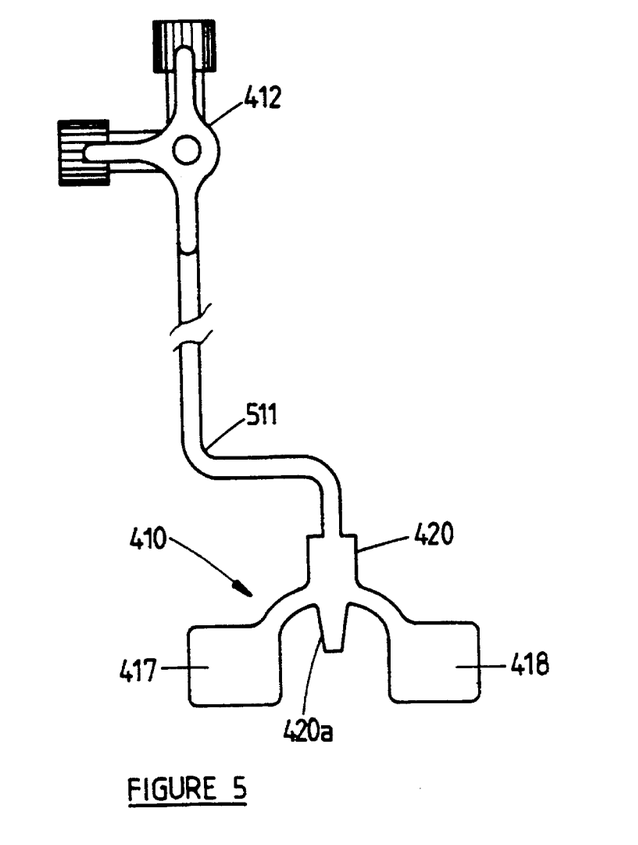
FIG. 5 is a plan view of a winged cannula connector fixed to a three-way tap with a length of flexible tubing fitted non-detachably between the tap and the connector.

Referring to FIGS. 4 and 5, there is shown a winged cannula connector 410 with wings 417, 418 and body 420 with spigot portion 420a fixed non-detachably to a three-way tap 412. FIG. 4 shows winged cannula connector 410 integrally formed with and directly attached to the three-way tap. FIG. 5 shows a winged cannula connector also fixed to a three-way tap, but with a length of flexible tubing 511 fitted non-detachably between the connector and the tap.

Figure 6:
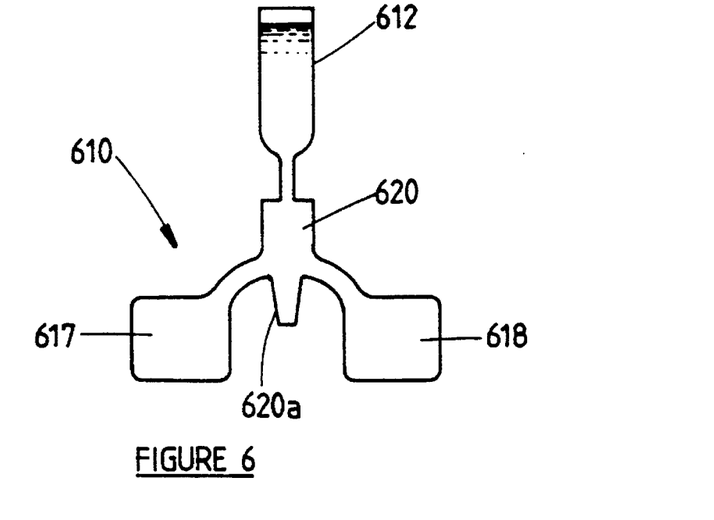
FIG. 6 is a plan view of a winged cannula connector fixed non-detachably to a non-return injection valve.
Figure 7:
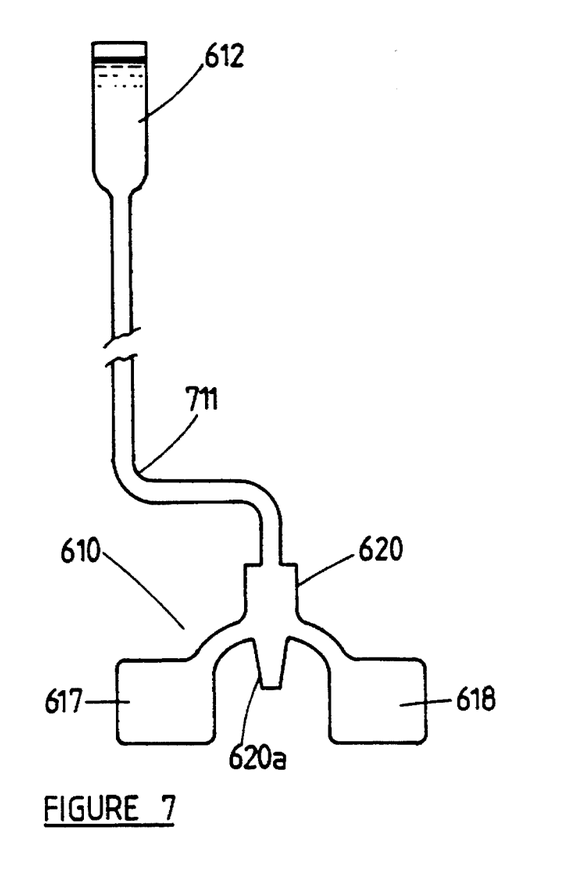
FIG. 7 is a plan view of a winged cannula connector fixed to a non-return injection valve with a length of flexible tubing fitted non-detachably between the valve and the connector.

FIGS. 6 and 7 show a winged cannula connector 610 with wings 617, 618, in which the body 620 with its spigot portion 620a is fixed non-detachably to a non-return injection valve 612. FIG. 6 shows the winged cannula connector 610 integrally formed with and directly attached to a non-return valve. FIG. 7 shows a winged cannula connector also fixed to a non-return valve, but with a length of flexible tubing 711 fitting non-detachably between the connector and the valve.

Figure 8:
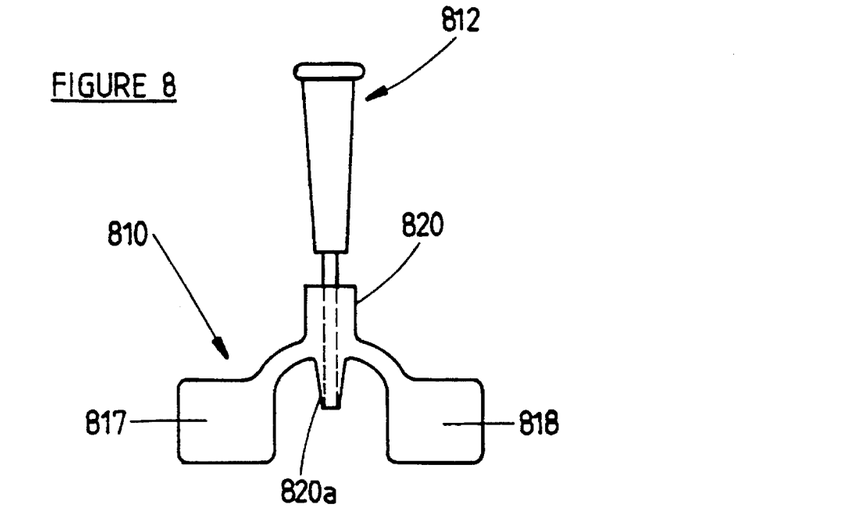
FIG. 8 is a plan view of a winged cannula connector fixed non-detachably to a plain luer attachment.
Figure 9:
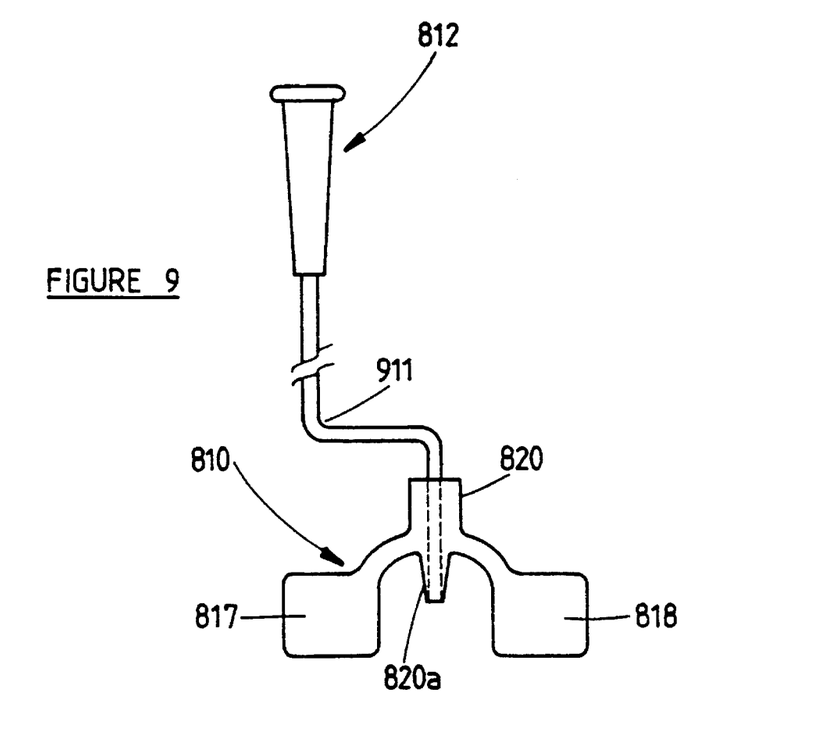
FIG. 9 is a plan view of a winged cannula connector fixed to a plain luer attachment with a length of flexible tubing fitted non-detachably between the luer attachment and the connector.

FIGS. 8 and 9 show a winged cannula connector 810 having wings 817, 818, in which the body 820 with its spigot 820a is fixed non-detachably to a standard luer fitting 812. FIG. 8 shows the winged cannula connector 820 integrally formed with and directly attached to the luer fitting. FIG. 9 shows the winged cannula connector also attached to a luer fitting but with a length of flexible tubing 911 fitted non-detachably between the connector and the luer fitting.

Figure 12:
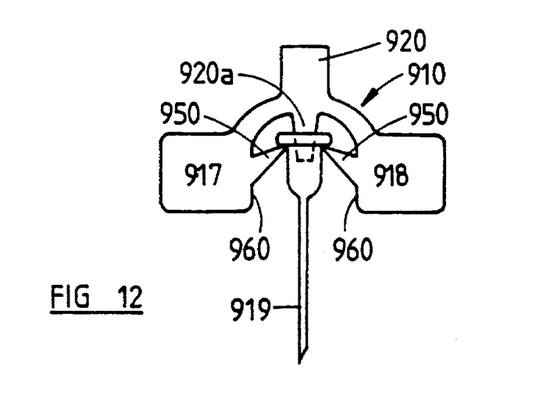
FIG. 12 is a plan view of a winged cannula connector, with a barbed step on the inside of the wings to improve the attachment of the spigot to the cannula socket.
Figure 13:
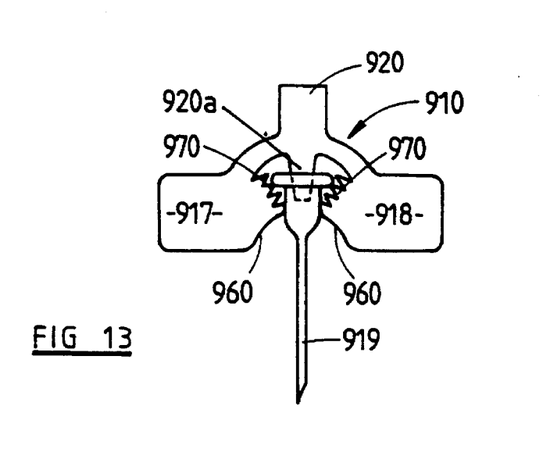
FIG. 13 is a plan view of a winged cannula connector with a ratchet-type grip on the inside of the wings to improve the attachment of the spigot to the cannula socket.
Figure 14:
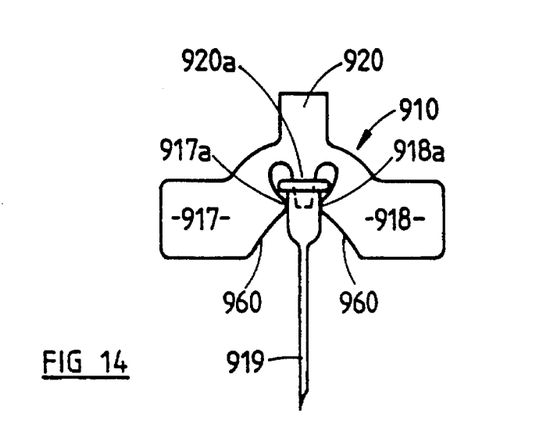
FIG. 14 is a plan view of a winged cannula connector with a textured protrusion of the inside of the wings to improve the attachment of the spigot to the cannula socket.

FIGS. 12, 13 and 14 show winged cannula connectors 910 where the structure of the inside edges 960 of the wings 917, 918, adjacent the body 920, has been adapted to improve the quality of attachment between the connector and the cannula 919, particularly at the socket end 921, so as to reduce the likelihood of disconnections. In FIG. 12 this has been achieved with barbed steps 950 on the edges 960 adjacent to but spaced from connector portion 920a of the connector 920. The steps 950 catch the proximal end of the cannula socket end 921 when engaged with the connector portion 920a. In FIG. 13 more secure attachment is achieved by ratchet-type grips 970 on the edges 960 which again catch the proximal end of the cannula socket. In FIG. 14 a similar result is achieved by suitably shaping the insides of the wings, together with the selection of an appropriately textured plastic, so as also to grip the proximal end of the cannula socket end. Particularly, the edges 917, 918 of the wings have convex formations 917a, 918a which effect the gripping.

Some advantages of the winged cannula connector described and of the wings being set forward to correspond with the socket portion of the pre-inserted cannula, are that of increased skin surface contact area, increased stabilisation of the cannula, improved and easier fixation of the cannula with the requirement of only a single piece of adhesive tape and the avoidance of pressure on the skin from the cannula. These wings also allow the use of a standard, non-winged cannula which may be easier to insert, and may improve the fixation of such cannulae to a spigot attachment, making disconnection less likely.

The embodiments of FIGS. 5, 7 and 9 each have a length of flexible tubing fitted non-detachably between their winged cannulae connectors 410, 610 and 810 and their various attachment fittings, a three-way tap 412, a non-return injection valve 612 and a standard luer fitting 812, respectively. The advantage of this tubing, when present, is that this will result in some "play" between a syringe attached to the attachment fitting concerned (412, 612, or 812) and its winged cannula connector. This will reduce the likelihood of dislodgment of the cannula by manipulation of the syringe, and also make it easier to detach the syringe from its attachment.

Figure 10:
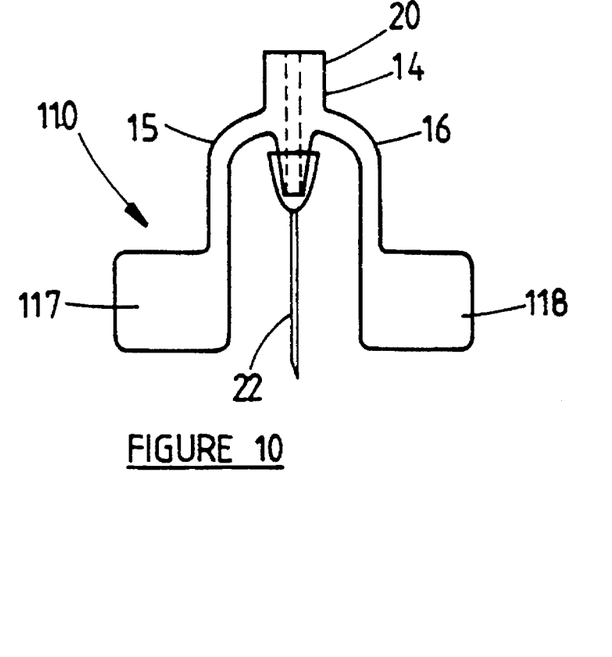
FIG. 10 is a plan view of a winged cannula connector with the wings positioned axially further forward relative to the cannula.

Referring to the embodiment of the winged cannula connector 110 shown in FIG. 10 of the drawings the wings 117, 118 are positioned axially further forward relative to the spigot of the cannula. This may provide improved fixation to the skin, and may also allow the connection of the spigot to the cannula socket to remain visible and accessible should this be desired.

Figure 11:
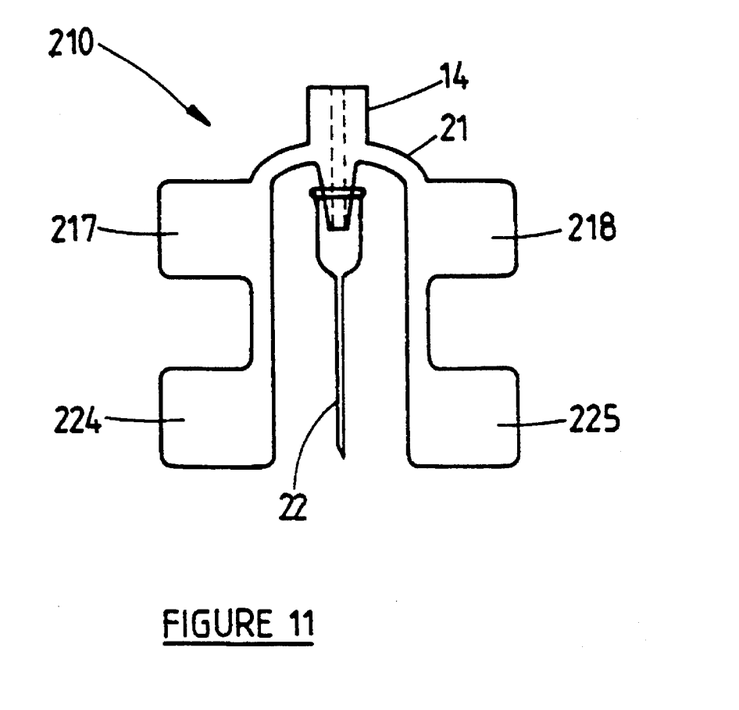
FIG. 11 is a plan view of a cannula connector with two sets of wings instead of one.

Referring to the embodiment shown in FIG. 11 of the drawings there is shown a cannula connector 210 with two sets of wings 217, 218 and 224, 225 which are also integrally moulded with the connector and which may provide improved fixation to the skin.

Whilst the embodiments apply to standard intravenous cannulae, the cannula connector could, with minor modifications, also be suitable for fixation of arterial lines, central venous lines, or hypodermic needles.

As an alternative construction, the spigot type cannula connector shown in the drawings could be replaced by a screw-on luer lock type connection.

It will be understood that the material and method of manufacture of the winged cannula connector and the number, exact shape, geometry, configuration and exact positioning of the wings relative to the body of the cannular connector according to the invention can be varied.

The described embodiments are advanced merely by way of explanation and any modifications and variations may be made without departing from the spirit and scope of the invention as defined in the appended claims.

I claim:

1. An intravenous cannula connector comprising:

(a) a body portion;

(b) a pair of lateral arm portions formed integrally with the body portion;

(c) a pair of flat wings set forward relative to the central body portion and connected to the lateral arm portions and adapted to facilitate taping of the cannula connector to the skin of a patient; and wherein the lateral arm portions and wing portions are formed integrally with the body portion.

2. The intravenous cannula connector according to claim 1, further adapted at one end of the body portion to couple to the end portion of the cannula.

3. The intravenous cannula connector according to claim 1, wherein the wings are substantially co-planer and coaxial with the body portion.

4. The intravenous cannula connector according to claim 1, wherein the wings are flexible.

5. The intravenous cannula connector according to claim 1, further comprising a structure on the inside edges of the wings to facilitate attachment of a cannula.

6. The cannula connector according to claim 5, wherein the structure comprises barbed steps.

7. The cannula connector according to claim 5, wherein the structure comprises ratchet-type grips.

8. A method of affixing a cannula connector and cannula to the skin of a patient, comprising:

(a) coupling a body portion of the cannula connector to said cannula; the body portion comprising a pair of lateral arm portions formed integrally with the body portion and a pair of flat wings set forward relative to the central body portion and connected to the lateral arm portions; and (b) securing the connector substantially flat against the skin with adhesive tape which extends over the lateral arm portions and flat wings.

9. The method according to claim 8, wherein flexible tubing is fitted between the connector and an intravenous or syringe attachment.

10. The method according to claim 9, wherein the intravenous or syringe attachment comprises a three-way, tap, non-return injection valve, or a plain female luer attachment.

11. The method according to claim 10, wherein the intravenous or syringe attachment comprises a plain female luer attachment.

12. A non-adhesive intravenous cannula connector comprising:

(a) a body portion; and (b) a pair of flat wings formed integrally with the body portion and set forward relative to and lateral to the central body portion, and adapted to facilitate taping of the cannula connector to the skin of a patient.

13. The intravenous cannula connector according to claim 12, further adapted at one end of the body portion to couple to the end portion of the cannula.

14. The intravenous cannula connector according to claim 12, wherein the wings are substantially co-planer and coaxial with the body portion.

15. The intravenous cannula connector according to claim 12, wherein the wings are flexible.

16. The intravenous cannula connector according to claim 12, further comprising a structure on the inside edges of the wings to facilitate attachment of a cannula.

17. The cannula connector according to claim 16, wherein the structure comprises barbed steps.

18. The cannula connector according to claim 16, wherein the structure comprises ratchet-type grips.

19. A method of affixing a cannula connector and cannula to the skin of a patient, comprising:

(a) coupling a body portion of the cannula connector to said cannula; the body portion comprising a pair of lateral flat wings formed integrally with the body portion and set forward relative to the central body portion; and (b) securing the connector substantially flat against the skin with adhesive tape which extends over the lateral flat wings.

20. The method according to claim 19, wherein flexible tubing is fitted between the connector and an intravenous or syringe attachment.

21. The method according to claim 20, wherein the intravenous or syringe attachment comprises a three-way, tap, non-return injection valve, or a plain female luer attachment.

22. The method according to claim 21, wherein the intravenous or syringe attachment comprises a plain female luer attachment.

\* \* \* \* \*